US012790210B2

(12) United States Patent
Edrees et al.

(10) Patent No.: US 12,790,210 B2
(45) Date of Patent: Nov. 10, 2026

(54) REACTOR WITH SUSTAINABLE POWER GENERATION

(71) Applicant: Saudi Arabian Oil Company, Dhahran (SA)

(72) Inventors: Rami Hatem Edrees, Dhahran (SA); Anas Bintin, Thuwal (SA); Issam Gereige, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 783 days.

(21) Appl. No.: 18/179,696

(22) Filed: Mar. 7, 2023

(65) Prior Publication Data

US 2024/0300812 A1 Sep. 12, 2024

(51) Int. Cl.

| | |
|---|---|
| ***C01B 3/38*** | (2026.01) |
| ***B01J 19/00*** | (2006.01) |
| ***C01B 3/047*** | (2026.01) |
| ***C01B 3/382*** | (2026.01) |
| ***C01B 21/02*** | (2006.01) |

(Continued)

(52) U.S. Cl.

CPC .......... *C01B 3/382* (2013.01); *B01J 19/0013* (2013.01); *C01B 3/047* (2013.01); *C01B 21/02* (2013.01); *C07C 4/04* (2013.01); *F24S 10/00* (2018.05); *B01J 2219/00054* (2013.01); *B01J 2219/00103* (2013.01); *C01B 2203/0233* (2013.01); *C01B 2203/0277* (2013.01); *C01B 2203/0833* (2013.01); *C01B 2203/1241* (2013.01); *C01B 2203/1614* (2013.01)

(58) Field of Classification Search

None

See application file for complete search history.

(56) References Cited

U.S. PATENT DOCUMENTS 9,011,560 B2 4/2015 Simmons et al.
9,651,313 B2 5/2017 Trainham et al.

(Continued)

FOREIGN PATENT DOCUMENTS

CN 210718166 U * 6/2020
WO WO 2012052661 4/2012

OTHER PUBLICATIONS

Chen et al. CN21071866U—translated document (Year: 2020).*

Albrecht et al., "Testing and Model Validation of a Prototype Moving Packed-Bed Particle-to-sCO2 Heat Exchanger," AIP Conference Proceedings, Dec. 2020, 9 pages.

Baumann et al., "Development and Performance Assessment of a Moving Bed Heat Exchanger for Solar Central Receiver Power Plants," Energy Procedia, May 2015, 69:748-57, 10 pages.

(Continued)

*Primary Examiner* — Jelitza M Perez

(74) *Attorney, Agent, or Firm* — Fish & Richardson P.C.

(57) ABSTRACT

A system includes a particle receiver, a heat exchanger, an electric generator, and a reactor. The particle receiver is configured to receive solar energy and transfer the solar energy to a heat transfer fluid. The heat exchanger is configured to transfer heat from the heat transfer fluid to a working fluid. The electric generator is configured to generate electrical power as the working fluid expands through the electric generator. The reactor includes a first compartment, a second compartment, and a heat transfer barrier. The heat transfer barrier is configured to transfer heat from the heat transfer fluid in the first compartment to the reaction feed stream in the second compartment, thereby maintaining an operating temperature of the reaction feed stream to at least a specified reaction temperature and converting at least one reactant in the reactant feed stream into at least one specified product.

20 Claims, 3 Drawing Sheets

(51) Int. Cl.

| | |
|---|---|
| ***C07C 4/04*** | (2006.01) |
| ***F24S 10/00*** | (2018.01) |

(56) References Cited

U.S. PATENT DOCUMENTS

| | | | | |
|---|---|---|---|---|
| 2013/0228163 | A1* | 9/2013 | Wait | B01J 19/24<br>126/714 |
| 2014/0298822 | A1* | 10/2014 | Ma | F03G 6/071<br>60/39.12 |
| 2014/0311479 | A1 | 10/2014 | Maryamchik et al. | |

OTHER PUBLICATIONS

Fuqiang et al., "Radiative Heat Transfer in Solar Thermochemical Particle Reactor: A Comprehensive Review" Renewable and Sustainable Energy Reviews, Feb. 2017, 73:935-49, 15 pages.

Gomez-Garcia et al., "Design and Performance of a Multistage Fluidised Bed Heat Exchanger for Particle-Receiver Solar Power Plants with Storage," Applied Energy, Jan. 2017, 190:510-523, 14 pages.

Meier, "A Predictive CFD Model for a Falling Particle Receiver/Reactor Exposed to Concentrated Sunlight," Chemical Engineering Science, 1999, 54:2899-2905, 7 pages.

Tan et al., "Review of Study on Solid Particle Solar Receivers," Renewable and Sustainable Energy Reviews, May 2009, 14:265-276, 12 pages.

* cited by examiner

REACTOR WITH SUSTAINABLE POWER GENERATION

TECHNICAL FIELD

This disclosure relates to reactors, and in particular, reactors powered by solar energy.

BACKGROUND

There is a growing interest in the energy transition from fossil fuels to renewable energy and sustainable energy in a global effort to reduce carbon emissions. Some examples of de-carbonization pathways in the energy transition to renewable energy include increasing energy usage efficiency, producing and/or using lower-carbon fuels, and carbon capture and storage. Alternatively, renewable energy sources can be utilized. Some examples of renewable energy sources include sunlight, wind, water movement, and geothermal heat. Most sources of renewable energy can be considered sustainable.

SUMMARY

This disclosure describes technologies relating to integration of solar energy utilization with reactors to produce chemical products and electrical power in a sustainable manner. Certain aspects of the subject matter described can be implemented as a system. The system includes a particle receiver, a heat exchanger, an electric generator, and a reactor. The particle receiver contains a heat transfer fluid. The heat transfer fluid includes a plurality of solid particles or molten salt. The particle receiver is configured to receive solar energy and transfer the solar energy to the heat transfer fluid, thereby heating the heat transfer fluid. The heat exchanger is downstream of the particle receiver. The heat exchanger is configured to transfer heat from the heat transfer fluid to a working fluid. The electric generator is configured to receive the working fluid and generate electrical power as the working fluid expands through the electric generator. The reactor includes a first compartment, a second compartment, and a heat transfer barrier. The first compartment is configured to receive the heat transfer fluid from the heat exchanger. The second compartment is configured to receive a reaction feed stream. The heat transfer barrier separates the first compartment from the second compartment. The heat transfer barrier is configured to transfer heat from the heat transfer fluid in the first compartment to the reaction feed stream in the second compartment, thereby maintaining an operating temperature of the reaction feed stream to at least a specified reaction temperature and converting at least one reactant in the reactant feed stream into at least one specified product.

This, and other aspects, can include one or more of the following features. The first compartment can be defined by a first pipe. The second compartment can be defined by an annulus between the first pipe and a second pipe. The second pipe can surround the first pipe. The heat transfer barrier can be a wall of the first pipe. The first compartment of the reactor can be in fluid communication with the particle receiver. The particle receiver can be configured to receive the heat transfer fluid from the first compartment for re-using the heat transfer fluid. The working fluid can include air. The particle receiver can be configured to heat the heat transfer fluid, via transfer of solar energy, to a first specified temperature in a range of from about 750 degrees Celsius (° C.) to about 1,000° C. The heat transfer fluid exiting the heat exchanger can have an operating temperature in a range of from about 600° C. to about 700° C. The reaction feed stream can include a hydrocarbon, carbon dioxide, ammonia, or any combinations of these. The system can include a catalyst disposed within the second compartment. The catalyst can be configured to, in response to contacting the reaction feed stream at a specified reaction temperature, accelerate a conversion of the at least one reactant in the reaction feed stream into the at least one specified product. The catalyst can include copper, nickel, iridium, molybdenum, cobalt, platinum, palladium, rhodium, ruthenium, or any combinations of these. The specified reaction temperature can be in a range of from about 400° C. to about 700° C.

Certain aspects of the subject matter described can be implemented as a method. Solar energy is transferred to a heat transfer fluid, thereby heating the heat transfer fluid. The heat transfer fluid includes solid particles or molten salt. After transferring solar energy to the heat transfer fluid, heat is transferred from the heat transfer fluid to a working fluid. After transferring heat from the heat transfer fluid to the working fluid, the working fluid is flowed to an electric generator. The electric generator generates electrical power as the working fluid expands through the electric generator. After transferring heat from the heat transfer fluid to the working fluid, the heat transfer fluid is flowed to a first compartment of a reactor. A reaction feed stream is flowed to a second compartment of the reactor. Heat is transferred from the heat transfer fluid in the first compartment to the reaction feed stream in the second compartment via a heat transfer barrier separating the first compartment from the second compartment, thereby maintaining an operating temperature of the reaction feed stream to at least a specified reaction temperature and converting at least one reactant in the reaction feed stream into at least one specified product.

This, and other aspects, can include one or more of the following features. The first compartment can be defined by a first pipe. The second compartment can be defined by an annulus between the first pipe and a second pipe. The second pipe can surround the first pipe. The heat transfer barrier can be a wall of the first pipe. The solar energy can be transferred to the heat transfer fluid by a particle receiver. The method can include recycling the heat transfer fluid from the first compartment of the reactor to the particle receiver for re-using the heat transfer fluid. The working fluid can include air. Transferring the solar energy to the heat transfer fluid can include heating the heat transfer fluid to a first specified temperature in a range of from about 750° C. to about 1,000° C. The heat transfer fluid exiting the heat exchanger can have an operating temperature in a range of from about 600° C. to about 700° C. The reaction feed stream can include a hydrocarbon, carbon dioxide, ammonia, or any combinations of these. A catalyst can be disposed within the second compartment. The catalyst can be configured to, in response to contacting the reaction feed stream at a specified reaction temperature, accelerate a conversion of the at least one reactant in the reaction feed stream into the at least one specified product. The catalyst can include copper, nickel, iridium, molybdenum, cobalt, platinum, palladium, rhodium, ruthenium, or any combinations of these. The specified reaction temperature can be in a range of from about 400° C. to about 700° C.

Certain aspects of the subject matter described can be implemented as a system. The system includes a particle receiver, a heat exchanger, an electric generator, and a reactor. The particle receiver contains a heat transfer fluid. The heat transfer fluid includes solid particles. The particle receiver is configured to receive solar energy and transfer the solar energy to the heat transfer fluid, thereby heating the heat transfer fluid to a first specified temperature in a range of from about 750° C. to about 1,200° C. The heat exchanger is downstream of the particle receiver. The heat exchanger is configured to transfer heat from the heat transfer fluid to a working fluid. The heat transfer fluid exiting the heat exchanger has an operating temperature in a range of from about 600° C. to about 700° C. The electric generator is configured to receive the working fluid and generate electrical power as the working fluid expands through the electric generator. The reactor includes a first pipe, a second pipe, and a catalyst. The first pipe is configured to receive the heat transfer fluid from the heat exchanger. The second pipe is configured to receive the reaction feed stream. The second pipe surrounds the first pipe. The catalyst is disposed within an annulus defined between the first pipe and the second pipe. The catalyst is configured to, in response to contacting the reaction feed stream at a specified reaction temperature, accelerate a conversion of at least one reactant in the reaction feed stream into at least one specified product. A wall of the first pipe is configured to transfer heat from the heat transfer fluid in the first pipe to the reaction feed stream in the second pipe, thereby maintaining an operating temperature of the reaction feed stream to at least the specified reaction temperature and producing the at least one specified product.

This, and other aspects, can include one or more of the following features. The first pipe of the reactor can be in fluid communication with the particle receiver. The particle receiver can be configured to receive the heat transfer fluid from the first pipe for re-using the heat transfer fluid.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes integration of a reactor with a particle receiver that utilizes concentrated solar power. The particle receiver concentrates and transfers solar energy to a heat transfer fluid (HTF) comprising solid particles or molten salt that can provide high temperature quality heat, for example, as high as about 1,200 degrees Celsius (° C.). The HTF can, for example, be used to generate power in gas turbines. After its use in power generation, the HTF effluent is typically at an operating temperature in a range of from about 600° C. to about 700° C. Process and heat integration can be implemented by utilizing this residual heat in a reactor (for example, a catalytic reactor). The heat provided to the reactor by the HTF effluent can be adjusted, for example, by adjusting one or more parameter of the particle receiver, such as max heating temperature of the particle receiver and/or the mass flow through the particle receiver. The systems and methods described here can be utilized in a residual heat utilization configuration (post power generation) or in a standalone concentrated solar power process in heating applications if determined to be economically feasible.

The subject matter described in this disclosure can be implemented in particular implementations, so as to realize one or more of the following advantages. The systems and methods described can partially or fully replace the use of fossil-based fuel with sustainable solar energy for power generation and/or production of chemical products. Thus, the systems and methods described can be implemented to reach or get closer to carbon neutrality and sustainability goals. The systems and methods described can be implemented as standalone, new units or be retrofitted to existing units to generate power and produce chemical products in a more sustainable manner. The systems and methods described can be implemented to produce chemical products via endothermic catalytic or non-catalytic reactions.

Figure 1A:
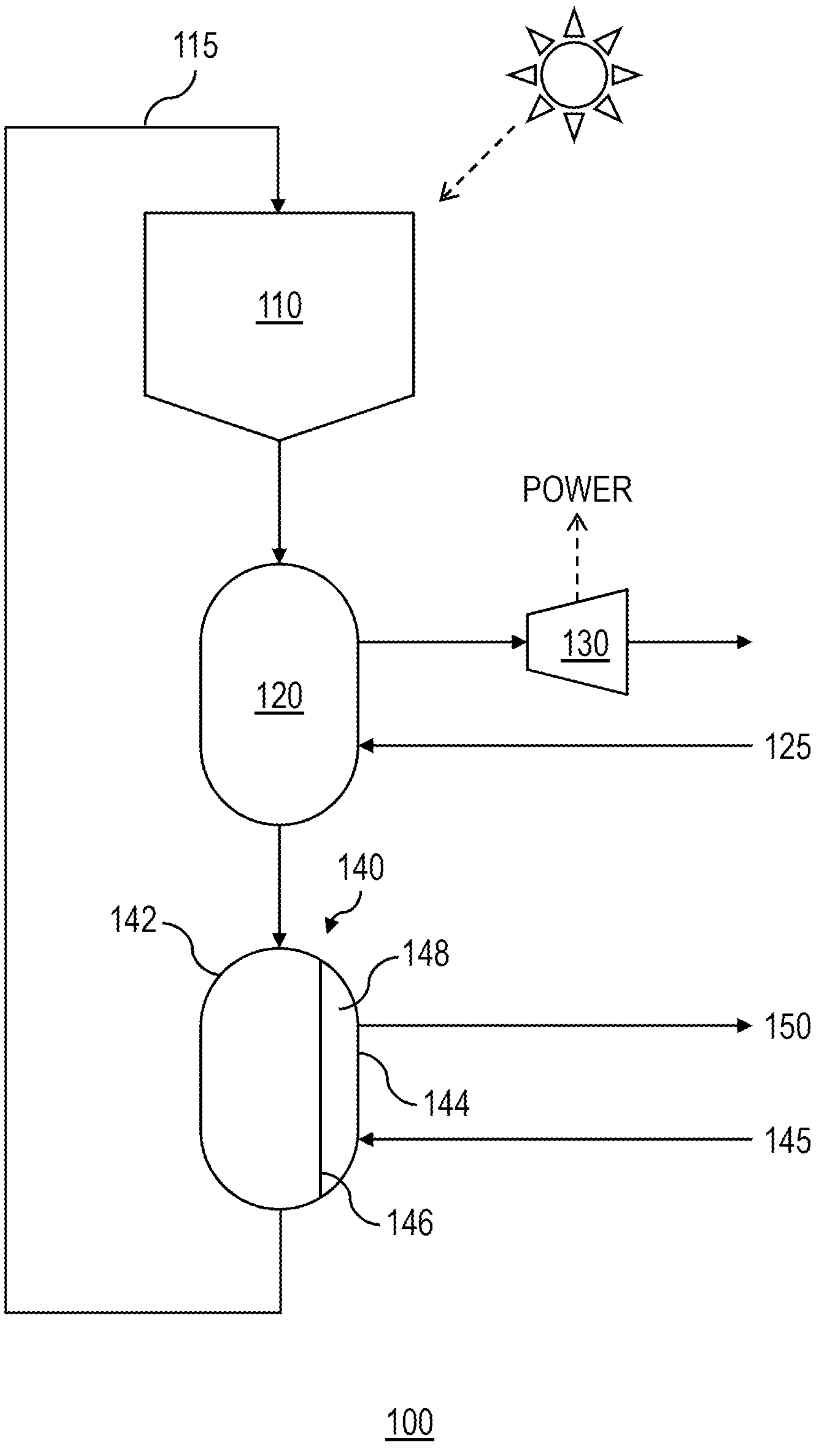
FIG. 1A is a schematic diagram of an example system that can utilize solar energy to generate electrical power and provide heat to an endothermic reactor.

FIG. 1A depicts an example system 100 that can utilize solar energy to generate electrical power and provide heat to an endothermic reactor. The system 100 includes a particle receiver 110, a heat exchanger 120, an electric generator 130, and a reactor 140. The particle receiver 110 contains a heat transfer fluid 115. The heat transfer fluid 115 is made of a material or a mixture of materials that are thermally stable at operating temperatures of up to about 1,200° C. In some implementations, the heat transfer fluid 115 is made of a material or a mixture of materials that is chemically inert. In some implementations, the heat transfer fluid 115 includes solid particles. For example, the heat transfer fluid 115 can include metal oxide(s). In some implementations, the heat transfer fluid 115 includes molten salt.

The particle receiver 110 is configured to receive solar energy from the sun and transfer the solar energy to the heat transfer fluid 115 as heat, thereby heating the heat transfer fluid 115. The particle receiver 110 can, for example, include a solar concentrator that receives solar energy and concentrates the received solar energy for more efficient heat transfer to the heat transfer fluid 115. In some implementations, the particle receiver 110 is configured to heat the heat transfer fluid 115 (via transfer of solar energy) to a first specified temperature in a range of from about from about 300° C. to about 1,200° C. or from about 700° C. to about 1,000° C. For example, the first specified temperature can be in a range of from about 300° C. to about 1,200° C., from about 350° C. to about 1,200° C., from about 400° C. to about 1,200° C., from about 450° C. to about 1,200° C., from about 500° C. to about 1,200° C., from about 550° C. to about 1,200° C., from about 600° C. to about 1,200° C., from about 650° C. to about 1,200° C., from about 700° C. to about 1,200° C., from about 750° C. to about 1,200° C., from about 800° C. to about 1,200° C., from about 850° C. to about 1,200° C., from about 900° C. to about 1,200° C., from about 950° C. to about 1,200° C., from about 1,000° C. to about 1,200° C., from about 1,050° C. to about 1,200° C., from about 1,100° C. to about 1,200° C., from about 1,150° C. to about 1,200° C., from about 700° C. to about 950° C., from about 750° C. to about 950° C., from about 800° C. to about 950° C., from about 850° C. to about 950° C., from about 900° C. to about 950° C., from about 700° C. to about 900° C., from about 750° C. to about 900° C., from about 800° C. to about 900° C., from about 850° C. to about 900° C., from about 700° C. to about 850° C., from about 750° C. to about 850° C., from about 800° C. to about 850° C., from about 700° C. to about 800° C., from about 750° C. to about 800° C., or from about 700° C. to about 750° C.

The heat exchanger 120 is located downstream of the particle receiver 110. The heat exchanger 120 is configured to transfer heat from the heat transfer fluid 115 to a working fluid 125. The heat exchanger 120 can be any suitable type of heat exchanger for transferring heat from the heat transfer fluid 115 to the working fluid 125. For example, the heat exchanger 120 can be a shell-and-tube heat exchanger, a double pipe heat exchanger, a plate-and-frame heat exchanger, a plate-fin heat exchanger, or a finned-tube heat exchanger. In some implementations, the heat transfer fluid 115 exiting the heat exchanger 120 has an operating temperature in a range of from about 300° C. to about 1,200° C. For example, the heat transfer fluid 115 exiting the heat exchanger 120 can have an operating temperature in a range of from about 400° C. to about 1,200° C., from about 500° C. to about 1,200° C., from about 600° C. to about 1,200° C., from about 700° C. to about 1,200° C., from about 800° C. to about 1,200° C., from about 900° C. to about 1,200° C., from about 1,000° C. to about 1,200° C., from about 1,100° C. to about 1,200° C. In some implementations, the heat transfer fluid 115 exiting the heat exchanger 120 has an operating temperature in a range of from about 600° C. to about 700° C. For example, the heat transfer fluid 115 exiting the heat exchanger 120 can have an operating temperature in a range of from about 600° C. to about 650° C., from about 650° C. to about 700° C., or from about 625° C. to about 675° C.

The electric generator 130 is configured to receive the working fluid 125 (that has been heated by the heat exchanger 120) and generate electrical power as the working fluid 125 expands through the electric generator 130. The electric generator 130 can, for example, include a turbine connected to a rotor surrounded by a stator. As the working fluid 125 flows across a turbine wheel of the turbine, the working fluid 125 expands and causes the turbine to rotate. The rotor rotates with the turbine, and the stator can convert the rotational energy of the rotor into electrical power. In some implementations, the working fluid 125 includes air, water (for example, steam), ammonia, or combinations thereof.

The reactor 140 is configured to receive the heat transfer fluid 115 from the heat exchanger 120 and receive heat from the heat transfer fluid 115 to maintain a reaction temperature for an endothermic reaction. The reactor 140 includes a first compartment 142, a second compartment 144, and a heat transfer barrier 146. In some implementations, the reactor 140 includes a catalyst 148. The heat transfer barrier 146 separates the first compartment 142 from the second compartment 144. The first compartment 142 is configured to receive the heat transfer fluid 115 from the heat exchanger 120. The second compartment 144 is configured to receive a reaction feed stream 145. The heat transfer barrier 146 is configured to transfer heat from the heat transfer fluid 115 in the first compartment 142 to the reaction feed stream 145 in the second compartment 144. The catalyst 148 can be disposed within the second compartment 144. The catalyst 148 is configured to accelerate a conversion of at least one reactant in the reaction feed stream 145 into at least one specified product. In cases where the desired chemical reaction can occur simply with heat input and without the use of the catalyst 148, the catalyst 148 can be omitted. Transferring heat from the heat transfer fluid 115 in the first compartment 142 to the reaction feed stream 145 in the second compartment 144 via the heat transfer barrier 146 increases and/or maintains an operating temperature of the reaction feed stream 145 to at least a specified reaction temperature. For example, the reactor 140 is configured to, by transferring heat from the heat transfer fluid 115 to the reaction feed stream 145 via the heat transfer barrier 146, maintain the operating temperature of the reaction feed stream 145 to be equal to or greater than the specified reaction temperature. The specified reaction temperature is a temperature at which the at least one reactant in the reaction feed stream 145 can be converted into the at least one specified product, such that the at least one specified product is produced at a desired conversion rate. The at least one specified product is discharged with a reaction product stream 150 from the second compartment 144 of the reactor 140.

The reactor 140 can be used to perform any endothermic reaction that can be carried out at a reaction temperature that is substantially equal to or less than the operating temperature of the heat transfer fluid 115 exiting the heat exchanger 120 (for example, about 700° C., about 650° C., about 600° C., or less than about 600° C.). In some implementations, the reactor 140 is a dry reforming reactor, in which the reaction feed stream 145 includes a hydrocarbon (such as methane) and carbon dioxide, and the catalyst 148 is a dry reforming catalyst that includes a noble metal, such as nickel or a nickel alloy. For dry reforming, the specified reaction temperature can, for example, be in a range of from about 400° C. to about 700° C., from about 450° C. to about 700° C., from about 500° C. to about 700° C., from about 550° C. to about 700° C., from about 600° C. to about 700° C., or from about 650° C. to about 700° C. For dry reforming, the products are carbon monoxide and hydrogen (the mixture is also known as syngas). The operating conditions (such as the specified reaction temperature), composition of the reaction feed stream 145, the catalyst 148, or a combination of these can be adjusted, for example, to maximize yield of a desired product, such as hydrogen.

In some implementations, the reactor 140 is a steam reforming reactor, in which the reaction feed stream 145 includes a hydrocarbon (such as methane) and water (for example, in the form of steam), and the catalyst 148 is a steam reforming catalyst that includes a metal, such as nickel or a nickel alloy. For steam reforming, the specified reaction temperature can, for example, be in a range of from about 400° C. to about 900° C., from about 450° C. to about 900° C., from about 500° C. to about 900° C., from about 550° C. to about 900° C., from about 600° C. to about 900° C., from about 650° C. to about 900° C., from about 700° C. to about 900° C., from about 750° C. to about 900° C., from about 800° C. to about 900° C., or from about 850° C. to about 900° C. For steam reforming, the products are carbon monoxide and hydrogen (syngas). The operating conditions (such as the specified reaction temperature), composition of the reaction feed stream 145, the catalyst 148, or a combination of these can be adjusted, for example, to maximize yield of a desired product, such as hydrogen.

In some implementations, the reactor 140 is an ammonia decomposition reactor, in which the reaction feed stream 145 includes ammonia, and the catalyst 148 is an ammonia decomposition catalyst that includes a metal (such as copper, nickel, iridium, molybdenum, cobalt, platinum, palladium, rhodium, or ruthenium), an alloy, a metal nitride, a metal carbide, a metal amide, or a metal imide. For ammonia decomposition, the specified reaction temperature can, for example, be in a range of from about 400° C. to about 700° C., from about 450° C. to about 700° C., from about 500° C. to about 700° C., from about 550° C. to about 700° C., from about 600° C. to about 700° C., or from about 650° C. to about 700° C. For ammonia decomposition, the products are nitrogen and hydrogen. The operating conditions (such as the specified reaction temperature), composition of the reaction feed stream 145, the catalyst 148, or a combination of these can be adjusted, for example, to maximize yield of a desired product, such as hydrogen or nitrogen, depending on market conditions.

In some implementations, the reactor 140 is a steam cracker, in which the reaction feed stream 145 includes a hydrocarbon (such as ethane, propane, butane, or any combinations thereof (for example, naphtha or liquefied petroleum gas)) and steam. In such cases, the catalyst 148 can be omitted. For steam cracking, the specified reaction temperature can, for example, be in a range of from about 400° C. to about 900° C., from about 450° C. to about 900° C., from about 500° C. to about 900° C., from about 550° C. to about 900° C., from about 600° C. to about 900° C., from about 650° C. to about 900° C., from about 700° C. to about 900° C., from about 750° C. to about 900° C., from about 800° C. to about 900° C., or from about 850° C. to about 900° C. For steam reforming, the products are hydrocarbons that are lighter than the hydrocarbon(s) present in the reaction feed stream 145. For example, the products are lower alkenes, such as ethylene and propylene. The operating conditions (such as the specified reaction temperature), composition of the reaction feed stream 145, or a combination of these can be adjusted, for example, to maximize yield of a desired product, such as ethylene.

As shown in FIG. 1A, the first compartment 142 is in fluid communication with the particle receiver 110. This configuration allows for the heat transfer fluid 115 to be recycled to the particle receiver 110 to be re-heated (by solar energy) and re-circulate through the system 100 to continue to provide heat to produce electrical power (via the electric generator 130) and to produce more reaction product (via the reactor 140). Although not shown in FIG. 1A, the system 100 can also include typical auxiliary components, such as separators, buffer containers, valves, pumps, vessels/tanks, blowers/compressors, and metering instruments. As an example, the system 100 can include a buffer container downstream of each of the particle receiver 110, the heat exchanger 120, and the reactor 140 for facilitating control of flow of the heat transfer fluid 115 circulating through the various components of the system 100.

Figure 1B:
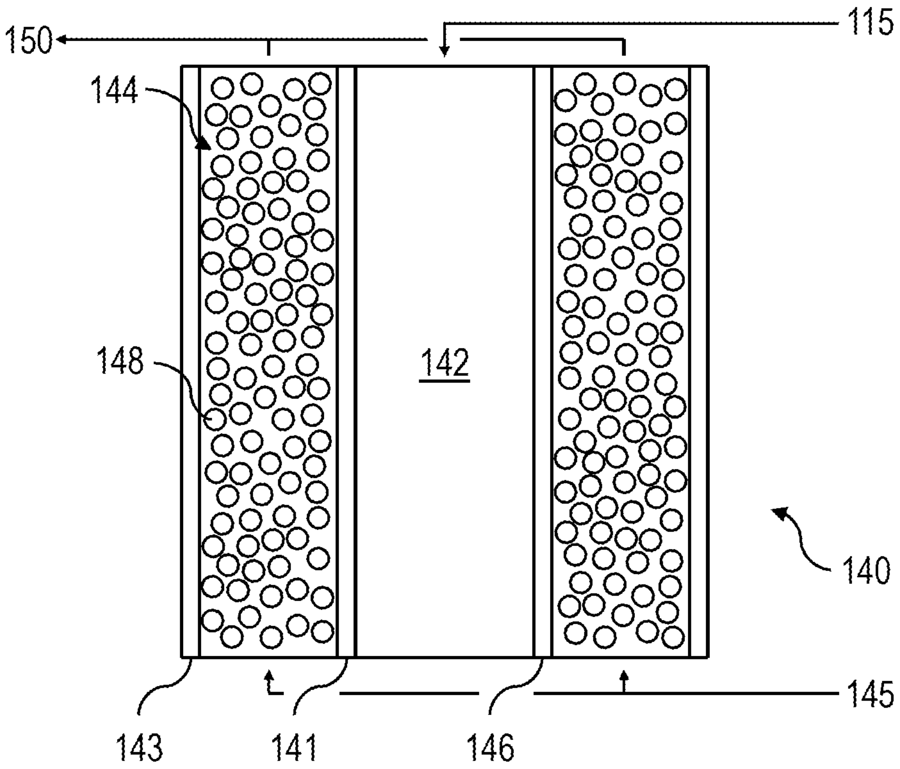
FIG. 1B is a vertical cross-sectional view of an example reactor that can be implemented in the system of FIG. 1A.
Figure 1C:
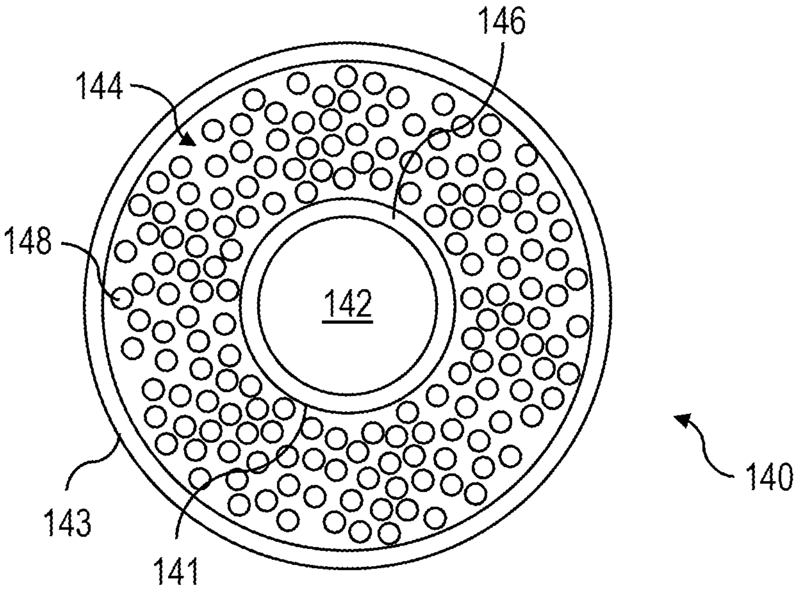
FIG. 1C is a horizontal cross-sectional view of the example reactor of FIG. 1B.

FIGS. 1B and 1C depict vertical and horizontal cross-sectional views, respectively, of an implementation of the reactor 140. In some implementations, as shown in FIGS. 1B and 1C, the reactor 140 is a double pipe reactor that includes a first pipe 141 and a second pipe 143. The second pipe 143 surrounds the first pipe 141. The first compartment 142 can be defined by the first pipe 141. For example, the first compartment 142 is an inner bore of the first pipe 141. The second compartment 144 can be defined by an annulus between the first pipe 141 and the second pipe 143. The catalyst 148 can reside in the annulus defined between the first pipe 141 and the second pipe 143. The heat transfer barrier 146 is the wall of the first pipe 141.

The heat transfer fluid 115 flows through the inner bore of the first pipe 141. The reaction feed stream 145 flows through the annulus between the first pipe 141 and the second pipe 143. In some implementations, the reactor 140 is in a parallel flow configuration, in which the heat transfer fluid 115 and the reaction feed stream 145 flow through the first pipe 141 and the annulus between the first pipe 141 and the second pipe 143, respectively, in generally the same direction. In some implementations, the reactor 140 is in a counter flow configuration, in which the heat transfer fluid 115 and the reaction feed stream 145 flow through the first pipe 141 and the annulus between the first pipe 141 and the second pipe 143, respectively, in generally opposite directions. In some implementations, the reactor 140 is in a cross flow configuration, in which the heat transfer fluid 115 and the reaction feed stream 145 flow through the first pipe 141 and the annulus between the first pipe 141 and the second pipe 143, respectively, in generally perpendicular directions. In some cases, the counter flow configuration can exhibit the greatest heat transfer efficiency out of these flow configurations (parallel, counter, and cross).

In some implementations, the catalyst 148 can instead reside in the first compartment 142, and the flow of the heat transfer fluid 115 and the reaction feed stream 145 can be switched between the first compartment 142 and the second compartment 144. For example, the catalyst 148 can reside in the inner bore of the first pipe 141, the reaction feed stream 145 can flow through the inner bore of the first pipe 141, and the heat transfer fluid 115 can flow through the annulus between the first pipe 141 and the second pipe 143. In such implementations, the second compartment 144 (as opposed to the first compartment 142) can be in fluid communication with the particle receiver 110 for recycling the heat transfer fluid 115 back to the particle receiver 110 for re-heating.

Figure 2:
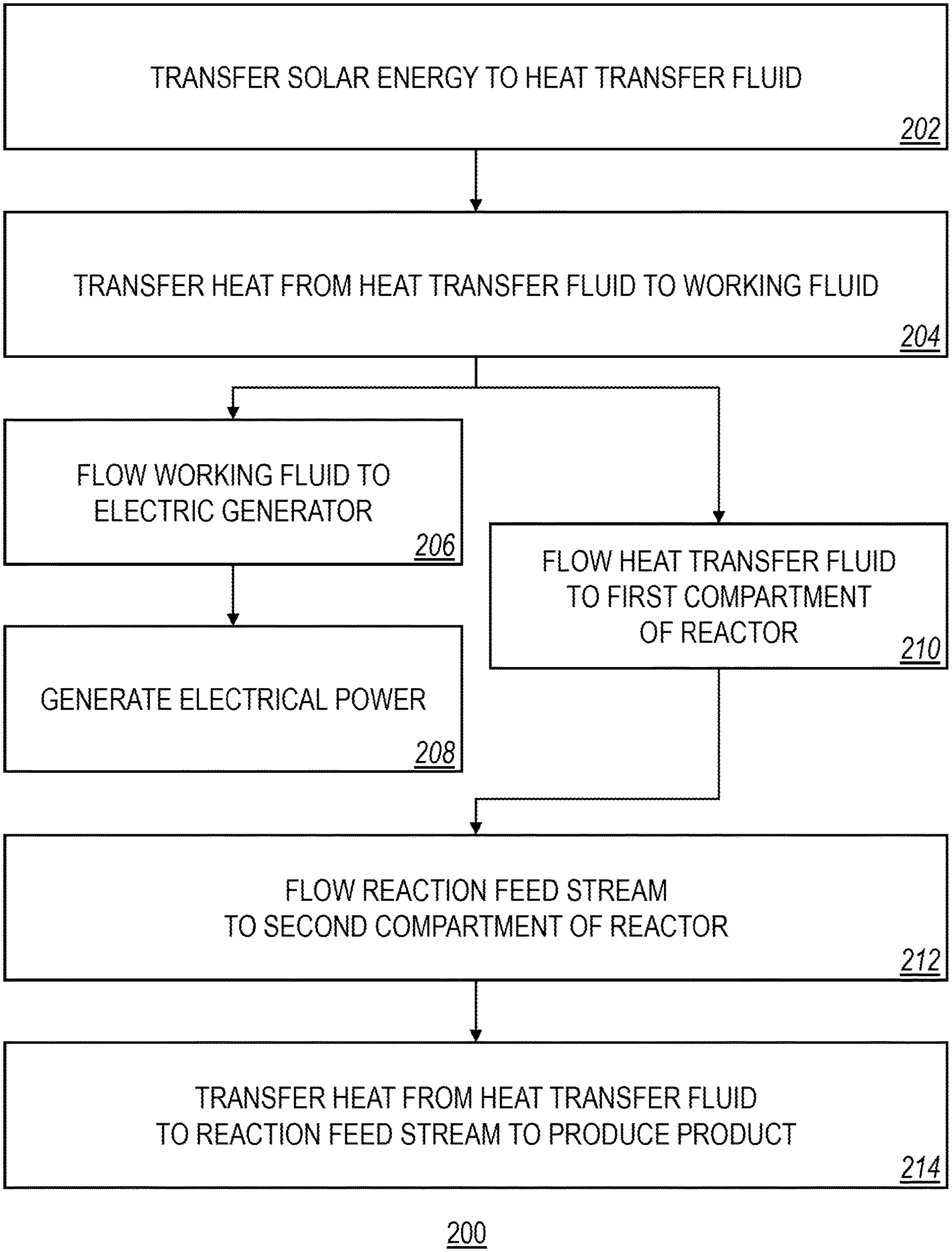
FIG. 2 is a flow chart of an example method for utilizing solar energy to generate electrical power and provide heat to an endothermic reactor.

FIG. 2 is a flow chart of an example method 200 for utilizing solar energy to generate electrical power and provide heat to an endothermic reactor (such as the reactor 140). The method 200 can, for example, be implemented by system 100. At block 202, solar energy is transferred to a heat transfer fluid (such as the heat transfer fluid 115), thereby heating the heat transfer fluid 115. The heat transfer fluid 115 can include solid particles, molten salt, or both. The solar energy can be transferred to the heat transfer fluid 115 at block 202, for example, by the particle receiver 110. At block 204, heat is transferred from the heat transfer fluid 115 to a working fluid (such as the working fluid 125). Heat can be transferred from the heat transfer fluid 115 to the working fluid 125 at block 204, for example, by the heat exchanger 120. At block 206, the working fluid 125 is flowed to an electric generator (such as the electric generator 130). At block 208, the electric generator 130 generates electrical power as the working fluid 125 expands through the electric generator 130. At block 210, the heat transfer fluid 115 is flowed to a first compartment of a reactor (such as the first compartment 142 of the reactor 140). At block 212, a reaction feed stream (such as the reaction feed stream 145) is flowed to a second compartment (such as the second compartment 144) of the reactor 140. As described previously, the catalyst 148 can be disposed within the second compartment 144, and the catalyst 148 is configured to, in response to contacting the reaction feed stream 145 at a specified reaction temperature, accelerate a conversion of at least one reactant in the reaction feed stream 145 into at least one specified product. At block 214, heat is transferred from the heat transfer fluid 115 in the first compartment 142 to the reaction feed stream 145 in the second compartment 144 via a heat transfer barrier (such as the heat transfer barrier 146). As described previously, the heat transfer barrier 146 separates the first compartment 142 of the reactor 140 from the second compartment 144 of the reactor 140. Transferring the heat from the heat transfer fluid 115 to the reaction feed stream 145 at block 214 maintains an operating temperature of the reaction feed stream 145 to at least the specified reaction temperature as the endothermic reaction takes place in the second compartment 144 and produces the at least one specified product. In some implementations, the method 200 includes recycling the heat transfer fluid 115 from the first compartment 142 of the reactor 140 to the particle receiver 110 for re-using the heat transfer fluid 115.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A system and comprising:

a particle receiver containing a heat transfer fluid comprising a plurality of solid particles, the particle receiver configured to receive solar energy and transfer the solar energy to the heat transfer fluid, thereby heating the heat transfer fluid;

a heat exchanger downstream of the particle receiver, the heat exchanger configured to transfer heat from the heat transfer fluid to a working fluid;

an electric generator configured to receive the working fluid and generate electrical power as the working fluid expands through the electric generator; and a reactor comprising:

a first compartment configured to receive the heat transfer fluid from the heat exchanger;

a second compartment configured to receive a reaction feed stream; and a heat transfer barrier separating the first compartment from the second compartment, the heat transfer barrier configured to transfer heat from the heat transfer fluid in the first compartment to the reaction feed stream in the second compartment, thereby maintaining an operating temperature of the reaction feed stream to at least a specified reaction temperature and converting at least one reactant in the reaction feed stream into at least one specified product; and a catalyst disposed within the second compartment, wherein the catalyst is configured to, in response to contacting the reaction feed stream at the specified reaction temperature, accelerate a conversion of the at least one reactant in the reaction feed stream into the at least one specified product.

2. The system of claim 1, wherein:

the first compartment is defined by a first pipe;

the second compartment is defined by an annulus between the first pipe and a second pipe;

the second pipe surrounds the first pipe; and the heat transfer barrier is a wall of the first pipe.

3. The system of claim 1, wherein the first compartment of the reactor is in fluid communication with the particle receiver, and the particle receiver is configured to receive the heat transfer fluid from the first compartment for re-using the heat transfer fluid.

4. The system of claim 1, wherein the working fluid comprises air.

5. The system of claim 1, wherein the particle receiver is configured to heat the heat transfer fluid, via transfer of solar energy, to a first specified temperature in a range of from about 750 degrees Celsius (° C.) to about 1,000° C.

6. The system of claim 5, wherein the heat transfer fluid exiting the heat exchanger has an operating temperature in a range of from about 600° C. to about 700° C.

7. The system of claim 6, wherein the reaction feed stream comprises a hydrocarbon, carbon dioxide, ammonia, or any combinations thereof.

8. The system of claim 1, wherein the catalyst comprises copper, nickel, iridium, molybdenum, cobalt, platinum, palladium, rhodium, ruthenium, or any combinations thereof.

9. The system of claim 8, wherein the specified reaction temperature is in a range of from about 400° C. to about 700° C.

10. A method comprising:

transferring solar energy to a heat transfer fluid, thereby heating the heat transfer fluid, wherein the heat transfer fluid comprises a plurality of solid particles or molten salt;

after transferring solar energy to the heat transfer fluid, transferring heat from the heat transfer fluid to a working fluid;

after transferring heat from the heat transfer fluid to the working fluid, flowing the working fluid to an electric generator;

generating, by the electric generator, electrical power as the working fluid expands through the electric generator;

after transferring heat from the heat transfer fluid to the working fluid, flowing the heat transfer fluid to a first compartment of a reactor;

flowing a reaction feed stream to a second compartment of the reactor;

transferring heat from the heat transfer fluid in the first compartment to the reaction feed stream in the second compartment via a heat transfer barrier separating the first compartment from the second compartment, thereby maintaining an operating temperature of the reaction feed stream to at least a specified reaction temperature and converting at least one reactant in the reaction feed stream into at least one specified product; and accelerating, with a catalyst is disposed within the second compartment in response to contacting the reaction feed stream at the specified reaction temperature, a conversion of the at least one reactant in the reaction feed stream into the at least one specified product.

11. The method of claim 10, wherein:

the first compartment is defined by a first pipe;

the second compartment is defined by an annulus between the first pipe and a second pipe;

the second pipe surrounds the first pipe; and the heat transfer barrier is a wall of the first pipe.

12. The method of claim 10, wherein the solar energy is transferred to the heat transfer fluid by a particle receiver, and the method comprises recycling the heat transfer fluid from the first compartment of the reactor to the particle receiver for re-using the heat transfer fluid.

13. The method of claim 10, wherein the working fluid comprises air.

14. The method of claim 10, wherein transferring the solar energy to the heat transfer fluid comprises heating the heat transfer fluid to a first specified temperature in a range of from about 750 degrees Celsius (° C.) to about 1,000° C.

15. The method of claim 10, wherein transferring heat from the heat transfer fluid to the working fluid comprises transferring heat in a heat exchanger, the heat transfer fluid exiting the heat exchanger has an operating temperature in a range of from about 600° C. to about 700° C.

16. The method of claim 15, wherein the reaction feed stream comprises a hydrocarbon, carbon dioxide, ammonia, or any combinations thereof.

17. The method of claim 15, wherein the catalyst comprises copper, nickel, iridium, molybdenum, cobalt, platinum, palladium, rhodium, ruthenium, or any combinations thereof.

18. The method of claim 17, wherein the specified reaction temperature is in a range of from about 400° C. to about 700° C.

19. A system comprising:

a particle receiver containing a heat transfer fluid comprising a plurality of solid particles, the particle receiver configured to receive solar energy and transfer the solar energy to the heat transfer fluid, thereby heating the heat transfer fluid to a first specified temperature in a range of from about 750 degrees Celsius (C) to about 1,200° C.;

a heat exchanger downstream of the particle receiver, the heat exchanger configured to transfer heat from the heat transfer fluid to a working fluid, wherein the heat transfer fluid exiting the heat exchanger has an operating temperature in a range of from about 600° C. to about 700° C.;

an electric generator configured to receive the working fluid and generate electrical power as the working fluid expands through the electric generator; and a reactor comprising:

a first pipe configured to receive the heat transfer fluid from the heat exchanger;

a second pipe configured to receive a reaction feed stream, the second pipe surrounding the first pipe; and a catalyst disposed within an annulus defined between the first pipe and the second pipe, the catalyst configured to, in response to contacting the reaction feed stream at a specified reaction temperature, accelerate a conversion of at least one reactant in the reaction feed stream into at least one specified product, wherein a wall of the first pipe is configured to transfer heat from the heat transfer fluid in the first pipe to the reaction feed stream in the second pipe, thereby maintaining an operating temperature of the reaction feed stream to at least the specified reaction temperature and producing the at least one specified product.

20. The system of claim 19, wherein the first pipe of the reactor is in fluid communication with the particle receiver, and the particle receiver is configured to receive the heat transfer fluid from the first pipe for re-using the heat transfer fluid.

* * * * *